US00PP31833P2

(12) United States Plant Patent
Scheiber

(10) Patent No.: US PP31,833 P2
(45) Date of Patent: Jun. 2, 2020

(54) ***VERONICA* PLANT NAMED 'BALMOOMAUI'**

(50) Latin Name: *Veronica spicata*
Varietal Denomination: Balmoomaui

(71) Applicant: Ball Horticultural Company, West Chicago, IL (US)

(72) Inventor: Sloane Michele Scheiber, Parkesburg, PA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/602,384

(22) Filed: Sep. 25, 2019

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Veronica* plant named 'Balmoomaui', characterized by its medium purple-colored flowers, dark green-colored foliage, and moderately vigorous, compact, upright-mounded growth habit, is disclosed.

1 Drawing Sheet

Latin name of genus and species of plant claimed: *Veronica spicata.*
Variety denomination: 'Balmoomaui'.

BACKGROUND OF THE INVENTION

The present invention relates to a new and distinct cultivar of *Veronica* plant botanically known as *Veronica spicata* and hereinafter referred to by the cultivar name 'Balmoomaui'.

The new cultivar originated in a controlled breeding program in Cochranville, Pa., during October 2013. The objective of the breeding program was the development of *Veronica* cultivars that flower without a vernalization requirement, have attractive and numerous inflorescences, and a compact, upright-mounded growth habit.

The new *Veronica* cultivar was the result of cross-pollination. The female (seed) parent of the new cultivar is MOODY BLUES Mauve 'Novavermau', U.S. Plant Pat. No. 26,621, characterized by its medium purple-colored flowers, dark green-colored foliage, and moderately vigorous, compact, upright-mounded growth habit. The male (pollen) parent of the new cultivar is MOODY BLUES Pink 'Novaverpin', U.S. Plant Pat. No. 25,748, characterized by its very pale purple-colored flowers, dark green-colored foliage, and moderately vigorous, compact, upright-mounded growth habit. The new cultivar was discovered and selected as a single flowering plant within the progeny of the above stated cross-pollination during June 2016 in a controlled environment in Cochranville, Pa.

Asexual reproduction of the new cultivar by terminal stem cuttings since June 2016 in Cochranville, Pa. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmoomaui' as a new and distinct cultivar of *Veronica* plant:

1. Medium purple-colored flowers;
2. Dark green-colored foliage; and
3. Moderately vigorous, compact, upright-mounded growth habit.

Plants of the new cultivar differ from plants of the female parent primarily in having less red coloration in the flower color. Plants of the new cultivar differ from plants of the male parent primarily in having a darker purple flower color.

Of the many commercially available *Veronica* cultivars, the most similar in comparison to the new cultivar is MOODY BLUES Dark Pink 'Balmoodink', co-pending application. However, in side-by-side comparisons, plants of the new cultivar differ from plants of 'Balmoodink' in at least the following characteristics:

1. Plants of the new cultivar have more purple coloration in the flower color than plants of 'Balmoodink';
2. Plants of the new cultivar have fewer inflorescences per plant than plants of 'Balmoodink'; and
3. Plants of the new cultivar have longer leaves than plants of 'Balmoodink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balmoomaui'. The plants were approximately four months old. The plants were grown as three plants per pot in one-gallon containers for approximately 11 weeks in a greenhouse in Elburn, Ill. followed by 3.5 weeks in an open-sided polyhouse in West Chicago, Ill. Plants were given one pinch at approximately one week before transplant.

DETAILED BOTANICAL DESCRIPTION

Figure 1:
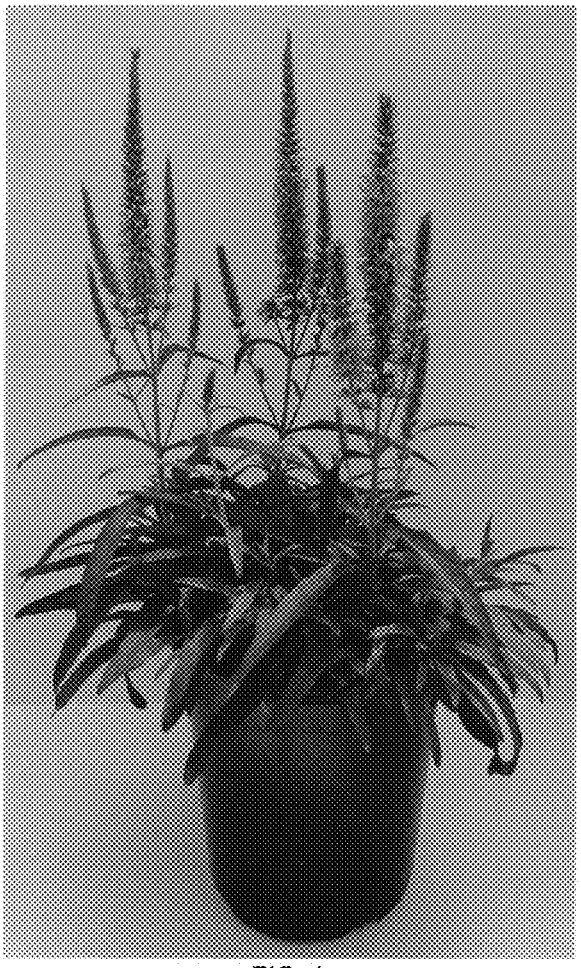
FIG. 1 illustrates a side view of the overall growth and flowering habit of 'Balmoomaui'.
Figure 2:
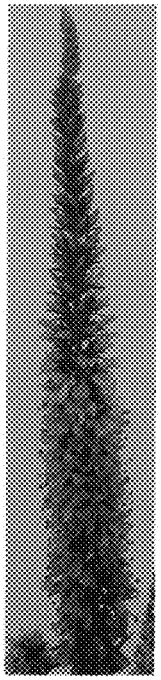
FIG. 2 illustrates a close-up view of the inflorescences of 'Balmoomaui'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2019 under natural light conditions in West Chicago, Ill.

The following descriptions and measurements describe approximately four-month old plants produced from cuttings from stock plants and grown under conditions comparable to those used in commercial practice. The plants were grown as three plants per pot in one-gallon containers for approximately 11 weeks in a greenhouse in Elburn, Ill. followed by 3.5 weeks in an open-sided polyhouse in West Chicago, Ill. Plants were given one pinch at approximately one week before transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Veronica spicata* 'Balmoomaui'.

Parentage:

*Female parent.*—MOODY BLUES Mauve 'Novavermau', U.S. Plant Pat. No. 26,621.

*Male parent.*—MOODY BLUES Pink 'Novaverpin', U.S. Plant Pat. No. 25,748.

Propagation:

*Type cutting.*—Terminal stem.

*Time to initiate roots.*—Approximately 7 to 10 days.

*Time to produce a rooted cutting.*—Approximately 35 to 42 days.

*Root description.*—Fibrous.

*Rooting habit.*—Freely branching.

Plant description:

*Commercial crop time.*—Approximately 10 to 12 weeks from a rooted cutting to finish in a 15 cm pot. Vernalization to initiate flowering is not required.

*Growth habit and general appearance.*—Herbaceous perennial, moderately vigorous, compact, upright-mounded.

*Hardiness.*—USDA Zone 4b (−25° F. to −20° F./−31.7° C. to −28.9° C.).

*Size.*—Height from soil level to top of plant plane: Approximately 38.0 cm. Width: Approximately 35.0 cm.

*Branching habit.*—Freely branching, pinching enhances basal branching. Quantity of main branches per plant: Approximately 3.

*Branch.*—Strength: Moderate. Branch height to bottom of inflorescence: Approximately 13.0 cm. Diameter: Approximately 4.0 mm. Length of central internode: Approximately 2.0 cm. Texture: Densely pubescent. Color of young stems: 146B. Color of mature stems: 146B, becoming woody 200D with age.

Foliage description:

*General description.*—Quantity of leaves per main branch: Approximately 14. Fragrance: None detected. Form: Simple. Arrangement: Opposite, decussate.

*Leaves.*—Aspect: Perpendicular to stem. Shape: Lanceolate. Margin: Serrate. Apex: Acute. Base: Attenuate. Venation pattern: Pinnate. Length of mature leaf: Approximately 9.5 cm. Width of mature leaf: Approximately 1.8 cm. Texture of upper surface: Moderately pubescent. Texture of lower surface: Moderately pubescent and densely pubescent on venation. Color of upper surface of young and mature foliage: Closest to NN137A. Color of lower surface of young and mature foliage: Closest to 138A. Venation of upper and lower surface: 147C.

*Petioles.*—Length: Approximately 1.7 cm. Width: Approximately 4.0 mm. Texture: Densely pubescent. Color: 147C.

Flowering description:

*Flowering habit.*—'Balmoomaui' is a long-day obligate, freely flowering under outdoor growing conditions blooming from early spring through autumn.

*Lastingness of individual flower on the plant.*—Approximately 7 days.

Inflorescence description:

*General description.*—Type: Terminal raceme, self-cleaning. Fragrance: None detected. Height: Approximately 12.0 cm to 18.0 cm. Width: Approximately 2.0 cm to 2.5 cm. Quantity per plant: Approximately 5.

*Peduncle.*—Strength: Strong. Aspect: Erect. Length: Approximately 3.0 cm to 5.0 cm. Diameter: Approximately 2.0 mm to 3.0 mm. Texture: Densely pubescent. Color: 146B.

Flower description:

*General description.*—Type: Single, salverform. Aspect: Outward. Quantity per inflorescence: Approximately 70.

*Bud.*—Rate of opening: Generally takes 3 to 4 days for bud to progress from first color to fully open flower.

*Bud just before opening.*—Shape: Oblong. Length: Approximately 6.0 mm. Diameter: Approximately 2.0 mm. Texture: Glabrous. Color: NN155D with an overlay of N82B.

*Corolla.*—Height: Approximately 9.0 mm. Diameter: Approximately 1.1 cm.

*Petals.*—Quantity: 4. Appearance: Dull. Shape: Elliptic. Margin: Entire, wavy. Apex: Broadly acute. Base: Fused into tube. Length: Approximately 5.0 mm to 6.0 mm. Width: Approximately 2.0 mm to 4.0 mm. Texture of upper and lower surfaces: Glabrous. Color of upper and lower surfaces when first open: N82C. Color of upper and lower surfaces when fully open N82B to N82C.

*Corolla tube.*—Length: Approximately 3.0 mm. Diameter at tube opening: Approximately 3.0 mm. Texture of inner surface: Densely pubescent. Color of pubescence: NN155D. Texture of outer surface: Glabrous. Color of inner surface: NN155D. Color of outer surface: N82D.

*Calyx.*—Shape: Cupped. Length: Approximately 5.0 mm. Diameter: Approximately 5.0 mm.

*Sepals.*—Quantity per flower: 4. Shape: Lanceolate, fused at base. Apex: Acute. Length: Two larger sepals approximately 5.0 mm and two smaller sepals approximately 4.0 mm. Width of all sepals: Approximately 1.0 mm. Texture of upper (inner) surface: Glabrous. Texture of lower (outer) surface: Moderately pubescent and densely pubescent on margins. Color of upper and lower surfaces: 137A with 146D at base.

*Pedicel.*—Strength: Strong, flexible. Aspect: Approximately 45° angle from peduncle. Length: Approximately 1.0 mm. Diameter: Approximately 0.5 mm. Texture: Densely pubescent with appressed and curled hairs. Color: 146B.

*Reproductive organs.*—Androecium: Stamen quantity: 2 per flower. Stamen length: Approximately 8.0 mm. Filament color: N82C. Anther shape: Sagittate, dorsifixed. Anther length: Approximately 1.0 mm. Anther color: 79B. Pollen amount: Abundant. Pollen color: 2D. Gynoecium: Pistil quantity: 1 per flower. Pistil length: Approximately 9.0 mm. Stigma shape: Rounded. Stigma length: Less than 1.0 mm. Stigma color: N82A. Style length: Approximately 8.0 mm. Style color: N82B. Ovary diameter: Approximately 1.0 mm. Ovary color: 145A.

Seed and fruit production: Neither seed nor fruit production has been observed.

Disease and pest resistance: Resistance to pathogens and pests common to *Veronica* has not been observed.

What is claimed is:

1. A new and distinct cultivar of *Veronica* plant named 'Balmoomaui', substantially as herein illustrated and described.

* * * * *